US006251371B1

(12) United States Patent
Holmen et al.

(10) Patent No.: US 6,251,371 B1
(45) Date of Patent: Jun. 26, 2001

(54) TREATMENT OF SKIN OR MUCOSA INFLAMMATION BY TOPICAL TREATMENT WITH PREPARATION CONTAINING DICHLOROBENZYL ALCOHOL

(75) Inventors: Hans Holmen, Broendby; Arne Martinus Pedersen, Vanloese, both of (DK)

(73) Assignee: Bifodan A/S, Hundested (DK)

( * ) Notice: Subject to any disclaimer, the term of this patent is extended or adjusted under 35 U.S.C. 154(b) by 0 days.

(21) Appl. No.: 09/341,427

(22) PCT Filed: Jan. 9, 1998

(86) PCT No.: PCT/DK98/00011
§ 371 Date: Aug. 30, 1999
§ 102(e) Date: Aug. 30, 1999

(87) PCT Pub. No.: WO98/30214
PCT Pub. Date: Jul. 16, 1998

(30) Foreign Application Priority Data

Jan. 9, 1997 (DK) .................................................. 0026/97

(51) Int. Cl.⁷ ........................... A61K 7/16; A61K 31/045; A61K 47/38
(52) U.S. Cl. ........................... 424/49; 514/724; 514/726; 514/817; 514/818; 514/829; 514/830; 514/862; 514/886; 514/887; 514/969
(58) Field of Search ................................ 424/49.58, 445, 424/488; 514/969, 862, 817, 818, 829, 830, 724, 726, 886, 887

(56) References Cited

U.S. PATENT DOCUMENTS

| 3,123,528 | * | 3/1964 | Fenton ................................... 167/55 |
| 3,982,022 | * | 9/1976 | Hool et al. ............................ 424/341 |
| 4,167,583 | * | 9/1979 | Knott et al. .......................... 424/343 |
| 4,656,031 | * | 4/1987 | Lane et al. ............................. 424/49 |
| 4,663,077 | * | 5/1987 | Rei et al. .............................. 252/364 |
| 5,708,023 | * | 1/1998 | Modak et al. ........................ 514/494 |
| 5,766,328 | * | 6/1998 | Nakabayashi et al. ................ 424/49 |
| 5,858,330 | * | 1/1999 | Boltri et al. ............................ 426/45 |
| 5,965,610 | * | 10/1999 | Modak et al. ........................ 514/494 |
| 5,989,527 | * | 11/1999 | Siegfried et al. ....................... 424/59 |
| 5,997,888 | * | 12/1999 | Weder et al. ......................... 424/401 |

FOREIGN PATENT DOCUMENTS

| 0 733 357 | 9/1996 | (EP) . |
| 92/18111 | 10/1992 | (WO) . |
| 95/26134 | 10/1995 | (WO) . |
| 96/32934 | 10/1996 | (WO) . |

OTHER PUBLICATIONS

Heim Theradie Der Tegennart 114(3): 411–422, 1975.*
Vorberg Therapre Der Tegenwart 116(10): 1896–1904, 1977.*
Wasilewski Therapie Der Tegenwart 115(117(: 1933–1940, 1976.*
Strick Therapie Der Te genwart 114(1): 71–81, 1975.*
Busman Therapie Woure 25(36): 4930–4934, 1975.*

* cited by examiner

Primary Examiner—Shep K. Rose
(74) Attorney, Agent, or Firm—Dykema Gossett PLLC

(57) ABSTRACT

The present invention relates to use of dichlorobenzyl alcohol for preparing a preparation for topical treatment of inflammation and the preparation for this purpose. It is known to use dichlorobenzyl alcohol (2,4-DCBA) as an agent against bacteria and fungi, i.e. as a disinfectant. By the present invention it has, however, surprisingly turned out that dichlorobenzyl alcohol, preferably 2,4-dichlorobenzyl alcohol, is also useful for treatment of inflammation. The invention also relates to a preparation containing dichlorobenzyl alcohol, preferably 2,4-dichlorobenzyl alcohol, for topical treatment of inflammation, which can be applied onto skin or mucosa in the form of an ointment, a cream, a gel or a solution. Thus, the preparation has turned out to be effective against a variety of inflammatory conditions including skin diseases, such as pruritus and psoriasis, insect bites and stings.

12 Claims, No Drawings

TREATMENT OF SKIN OR MUCOSA INFLAMMATION BY TOPICAL TREATMENT WITH PREPARATION CONTAINING DICHLOROBENZYL ALCOHOL

BACKGROUND OF THE INVENTION

1. Field of the Invention

The present invention relates to diclorobenzyl alcohol, containing preparations.

2. The Prior Art

It is known to use 2,4-dichlorobenzyl alcohol (hereinafter referred to as 2,4-DCBA) as a bactericidal and/or fungicidal agent against a variety of bacteria and fungi, including yeast, mould fungi, fungi in the skin, and a number of gram-positive and gram-negative bacteria. Thus, it has been known to use 2,4-DCBA in combination with other bactericidal agents in antiseptic lozenges for more than 30 years.

2,4-DCBA has also successfully been used as an antimicrobial agent for treatment of infections in mouth and throat, in antiseptic skin preparations for disinfection and treatment of minor cuts and abrasions, and foot creams/lotions for treatment of fungi.

U.S. Pat. No. 3,123,528 discloses a pharmaceutical preparation for oral use which includes 2,4-DCBA and a pharmaceutically acceptable diluent or carrier. The compositions inter alia include mouth washes, toothpastes, pastilles, lozenges, lotions, eardrops, which compositions are used for combating infections caused by bacteria and fungi in ear, throat and skin. If desired, the composition may also contain saligenin (o-hydroxy-benzyl alcohol) which is a local anaesthetic, incorporated in order to impart both bactericidal and anaesthetic effect to compositions for oral use.

EP patent application No. 161 898 discloses dentrifice compositions, including tooth creams and tooth gels, and which comprise a bactericidal agent for treatment of plaque (bacteria coatings), e.g. 2,4-DCBA.

Further, U.S. Pat. No. 4,167,583 discloses antimicrobial compositions for disinfection of the skin of humans and animals, which compositions inter alia may contain dichlorobenzyl alcohol, e.g. 2,4-DCBA. The compositions may also be used for disinfection of surgical instruments and equipment. The compositions are particularly suited for disinfection of hands, e.g. in case of surgery.

WO 95/26134 discloses a composition for application onto a surface, such as the surface of an apparatus or an instrument, a dressing, a glove, a condom or a skin surface, and comprising an agent for inactivating a so-called irritant and a substance which effectively prevents the irritant-inactivating agent from binding to the surface. Antimicrobial agents, including 2,4-DCBA, are mentioned as examples of irritant-inactivating agents.

WO 92/1811 discloses the use of an antimicrobial agent, such as 2,4-DCBA, for preparing a preparation for treatment of gastric disorders caused by the microorganism *Helicobacter pylori*.

WO 96/32934 discloses the use of a composition comprising 2,4-DCBA and amylmetacresol for preparing a medicament for the treatment or prevention of HIV viral infections.

EP 0 733 357 discloses topical pharmaceutical formulations in the form of a thixotropic gel, which formulation besides an active component contains from 2 to 15% of colloidal silica, water and optionally one or more excipients. As examples of active components, mention is made of non-steroidal anti-inflammatory agents and anti-bacterials/antibiotics. I.a. a formulation containing 2,4-DCBA is mentioned.

Further, it is known to use 2,4-DCBA in order to prevent bacterial/fungal growth in e.g. cosmetics, toilet ware, including shampoos and antiplaque toothpastes, household articles, textiles, timber, leather goods, paper etc.

SUMMARY OF THE INVENTION

The invention is based on the discovery that dichlorobenzyl alcohol, and in particular 2,4-DCBA, has a surprisingly good effect on inflammations.

An inflammation is the result of an extraneously provoked damage to cells or tissue. Such damages can be provoked by chemical and/or physical influences on the skin of humans and animals. Examples of physical influences are strokes, heat, cold, radiation and electrical chock, and examples of chemical influences are contact with acids, bases and allergens. Inflammation may also be provoked by microorganisms acting on the skin, as opposed to infections which are the result of microorganisms invading the human or animal body.

In other words, inflammation is a defense mechanism caused by extraneously provoked influences on skin or tissue. The symptoms may be one or more of the following: pain, increased surface temperature, swelling, erythema and reduced or ceased function, e.g., masticating efficiency.

Thus, the invention relates to the use of dichlorobenzyl alcohol, and in particular 2,4-DCBA, for preparing a preparation for topical treatment of inflammation.

Use of 2,4-DCBA in low concentrations has turned out not to have an irritating (inflammatory) effect on skin and mucosa. Reactions on the skin have been studied by directly applying solutions in propylene glycol under a dressing on the stomach of guinea pigs for 4–5 hours. Concentrations of up to 1% caused no or little damage, while higher concentrations caused inflammatory conditions.

In spite of 2,4-DCBA having very limited solubility in water, the substance may effectively be incorporated into aqueous systems. The solubility in organic solvents is good.

When treating an inflammatory condition, dichlorobenzyl alcohol, preferably 2,4-DCBA, can be applied onto skin or mucosa in the form of an ointment, cream, a gel or a solution.

In order for the active compound (dichlorobenzyl alcohol, 2,4-DCBA) to have the optimum effect, it is important that it be retained at the inflammatory site for prolonged time. For this purpose bioadhesives may advantageously be used, which are substances binding to biological materials, including proteins, cells or tissue. A bioadhesive may consequently be defined as a compound capable of binding to the biological material and remain bound for a given period of time. When the biological material is mucosa, it is a matter of mucoadhesive materials. Mucoadhesive materials in the form of polymers are normally capable of forming hydrogels.

In one embodiment of the invention, the active compound is combined with one or more substances which provide a controlled release and/or a prolonged retention of dichlorobenzyl alcohol at the treatment site.

In a further embodiment of the invention, the active compound is combined with one or more bioadhesive materials.

Examples of bioadhesive materials include hydrocolloids, such as sodium carboxymethylcellulose, Carbopol, Tragacanth, Karaya gum, sodium alginate, gelatin, methylcellulose and gum arabic.

It is characteristic of bioadhesive materials that they are macromolecular organic hydrocolloids with hydrophilic, functional groups capable of forming hydrogen bonds with, e.g., the corresponding functional groups on the biological material. The strength of the bioadhesive material increases when the molecular weight is increased to more than 100 000 Dalton.

By using bioadhesives, the retention time of the active agent on the ad/absorbing surface is prolonged, as mentioned above. Many different types of bioadhesive materials, both natural and synthetic, can be used for controlling the release of the active agent.

The compound 2,4-DCBA has turned out to be effective against various skin diseases, including pruritus and psoriasis. Further, the compound has turned out to be effective for treatment of insect bite/sting (inflammatory conditions).

The invention also relates to a preparation for topical treatment of inflammation which can be applied onto skin and/or mucosa, and which as active component contains dichlorobenzyl alcohol.

In an embodiment of the preparation it includes, besides the active component, a bioadhesive thickening agent and water.

In a preferred embodiment of the preparation it is formed of 0.05–2 weight-%, preferably about 1 weight-%, of dichlorobenzyl alcohol, 0.1–10 weight-%, preferably about 2 weight-%, of bioadhesive material, and 90–99 weight-%, preferably about 97 weight-%, of water.

As the new preparation is both disinfecting, anti-inflammatory and pain-relieving, and when applied for oral use in the form of a dentrifice composition, it is useful for treatment and pain-relief in a variety of conditions, e.g., paradentosis, inflammation around erupting wisdom teeth, following extraction of teeth, for prophylactic disinfection of the oral cavity of sick patients who are not themselves capable of taking care of sufficient dental hygiene, parodontal abscesses, prosthesis induced pressure sores on the mucosa, fungal infections and for treating exposed bone surface in alveolitis sicca dolorosa, which is a painful condition which may arise following extraction of teeth.

The dentrifice composition may, depending of the content of thickening agent (bioadhesive), be formulated as a mouth wash or a tooth gel. When the dentrifice composition is formulated as a tooth gel, the thickening agent together with water forms a gel phase in which undissolved particles of the active agent, e.g., 2,4-DCBA, are dispersed.

In the following the invention is described in more detail with reference to the following examples.

EXAMPLE 1

The effect of a preparation according to the invention on oral inflammation was tested clinically.

For the clinical examination a preparation containing 2,4-DCBA (Myracid SP), sodium carboxymethylcellulose Ph.Eur. and Aqua purificata Ph.Eur. was prepared in three variants:

Mouth Wash

| | |
|---|---|
| 1. 2,4-dichlorobenzyl alcohol (Myacid SP) | 5 g |
| 2. Sodium carboxymethylcellulose Ph.Eur. | 0.9 g |
| 3. Aqua purificata Ph.Eur. | 994.1 g |

Tooth Gel (Thin)

| | |
|---|---|
| 1. 2,4-dichlorobenzyl alcohol (Myacid SP) | 1% |
| 2. Sodium carboxymethylcellulose Ph.Eur. | 2% |
| 3. Aqua purificata Ph.Eur. | 97% |

The above percentages are in weight-%.

Tooth Gel (Thick)

| | |
|---|---|
| 1. 2,4-dichlorobenzyl alcohol (Myacid SP) | 1% |
| 2. Sodium carboxymethylcellulose Ph.Eur. | 4% |
| 3. Aqua purificata Ph.Eur. | 95% |

The above percentages are in weight-%.

The two variants of the gel were filled into tubes having a rectal tip in order to facilitate the application to the patients. The mouth wash was dispensed in bottles with appertaining dosage cup.

The patients for the examination were recruited by five privately practising dentists.

Inclusion criteria for treatment with the gel: Patients over the age of 18 with oral inflammatory conditions who had not responded to conventional treatment. Additionally, it was a requirement that the individual patient was a regular patient of the dentist performing the treatment.

Exclusion criteria: Patients exclusively being treated in acute emergency treatment. Patients under the age of 18.

The treatment of the patients with the three variants of the preparation consisted partly in a local application at the dentist, partly in dispensing the preparation for home use by the patient himself.

Approx. 60 patients participated in the examination, of which 41 answered a handed out questionnaire (see questionnaire 1).

The majority of the patients felt pain or soreness in connection with the condition in question for which they were to be treated.

The result of the examination was that 39 patients had noted a beneficial effect from the preparation. As regards the majority of the patients this effect occurred almost instantaneously, while the effect occurred in the course of the first day as regards the remaining part of the patients. 2 patients with total paradentosis, however, could register no effect. No patients reported discomfort during or after the treatment.

Besides using the gel for inflammatory conditions in the oral cavity some of the patients also used the gel for treatment of dermal inflammatory conditions following bee sting and mosquito bite, contact allergies, mechanical/physical traumas and various chemical actions. Also for treatment of these conditions the preparation turned out to have a beneficial effect (see questionnaire 2).

The dentists performing the treatment agreed that the preparation was easily applicable and had a good adhesive capacity. The dentists had used the gel for treatment of inflammatory conditions in mouth and throat. All types of inflammation showed a positive response, both as regards pain, erythema, swelling, heat and reduced function, e.g., reduced masticating efficiency. In connection with wounds the gel turned out to have a marked healing effect.

Based on the results of the clinical examination and the dentists' own observations it can be concluded that the gel is extremely suitable for treatment of inflammation. Since the healing of e.g., mechanical traumas is promoted by the preparation, the risk of secondary infections is reduced.

The pain-relieving effect of the preparation is of great value in the treatment of inflammatory conditions. This applies both to the physical aspect and also highly to the psychical aspect, since absence of, e.g., pain is of great importance when adapting/adjusting to a new prosthesis. In such situations the problem is often that irritation (inflammation) of the mucosa and also maybe wound formation occur, for which reason the patient is disinclined to use the prosthesis because of pain, which often has consequences in the form of changes of the underlying bone structure or teeth migrations, in cases where it is a question of adaptation of/to partial prostheses.

Questionnaire 1

Questionnaire for the patients (41 patients)

What symptoms did you yourself feel before the last dental visit?

| | |
|---|---|
| Pain or soreness | 34 (83%) |
| One or more teeth were "loose" | 4 (10%) |
| Difficulty of chewing | 6 (15%) |
| Bleeding when brushing teeth | 7 (17%) |
| Sores on gums, tongue or the like | 6 (15%) |
| Sores in the corners of the mouth | 3 (7%) |
| Burning of e.g. the palate | 3 (7%) |
| Other discomfort¤ | 7 (17%) |

¤alveolitis sicca 5 patients, candida infection 2 patients

Did you feel any effect of the treatment with the mouth wash or the tooth gel?

| | |
|---|---|
| Yes: 39 (95%) | No: 2 (5%) |

If you felt any effect of the treatment how soon then did the effect occur after the start of the treatment?

| | |
|---|---|
| Almost instantaneously | 32 (78%) |
| In the course of the first day | 7 (17%) |
| Later on in the course of treatment | 2 (5%)¤ |

¤in the course of the first week

Did you feel any discomfort during or after the treatment with the mouth wash or the tooth gel?

Yes: 1 (2%) ¤

No: 40 (98%)

¤ the taste is not good!

Primarily, I was treated with:

| | |
|---|---|
| Mouth wash | 8 (20%) |
| Tooth gel | 15 (37%) |
| By an large equal amounts | 18 (44%) |

Questionnaire 2

Treatment of Dermal Inflammatory Conditions (The figures indicate number of persons irrespective of how many times the preparation has been used by the same user)

| | |
|---|---|
| Mosquito bite | 8 |
| bee sting | 3 |
| Fleabite | 1 |
| Sun burn | 2 |
| Heat eczema | 1 |
| Contact allergy | 3 |
| Psoriasis | 2 |
| Erysipelas | 1 |
| Acne | 2 |
| Inflammatory condition at nails | 3 |
| Cuts | 3 |
| Burns from oven or hot-plate | 3 |
| Total | 32 |

All persons reported beneficial effect

EXAMPLE 2

In order to substantiate the results mentioned in example 1 of a clinical examination of 2,4-DCBA's anti-inflammatory effect, a controlled laboratory examination was performed.

It was the object of this laboratory examination to measure the anti-inflammatory effect of 2,4-DCBA against a chronic, toxic skin inflammation in mice ears induced by 12-O-tetradecanoyl-phorbol-13-acetate (TPA).

The mice had been selected as test objects after having been found suited for ear irritation studies.

As carrier for the test substance, 2,4-DCBA, acetone is used, which as a matter of routine is used in mice ear experiments of the type in question.

24 female mice are used having a body weight of between 19 and 22 g at the start of the examination. The mice were kept in an animal stable with air filtration and a room temperature of 24° C.+/−3° C., a relative air humidity of 55%+/−15% and air change 10 times per h. The illumination of the room followed a 24 h cycle with 12 h of light and 12 h of darkness. Thus, the light was on from 6 o'clock to 18 o'clock.

The mice were kept in groups in polycarbonate cages having an area of 810 $cm^2$. The cages were cleaned and the underlayer replaced at least 3 times a week. The underlayer was saw dust. Analyses for determination of any contamination were conducted regularly.

The mice had free access to food in the form of "altromin 1314"-pellets and bottles with water added with hydrochloric acid to achieve a pH-value of 2.5.

Both the solid and the liquid food was examined regularly for contamination.

The mice were divided into 4 groups according to a principle of randomness and were tail tagged.

The groups and the animal numbers were as follows:

| Group | Treatment | Animal number | Colour code |
|---|---|---|---|
| 1 | Naive control | 1–6 | White |
| 2 | Inflammation control | 7–12 | Blue |
| 3 | Test substance | 13–18 | Green |
| 4 | Positive control | 19–24 | Red |

Group 1 was given neither TPA nor 2,4-DCBA

Group 2 was induced with TPA, but was not treated with 2,4-DCBA.

Group 3 was the real test group, which was induced with TPA and treated with 2,4-DCBA.

Group 4 was a positive control group, which was induced with TPA and subsequently treated with a known anti-inflammatory substance, betamethasone valerate.

It is noted that group 4 was only included in order to demonstrate the validity of the examination model. Thus, the aim was not to compare effects of 2,4-DCBA with the known potently acting antiinflammatory betamethasone valerate.

The mice in groups 2–4 were induced with 0.1 ml of TPA solution (0.1 mg/ml) in the left ear on day 1, 3, 5, 7 and 9, whereby a toxic inflammation developed. On day 8, 9, 10 and 11 the mice in the groups 3 and 4 were treated with 2,4-DCBA (0.1 ml/ear of the 1% solution) and the control preparation (0.1 ml/ear), respectively, twice a day on the left ear.

6 hours after the treatment on day 11 the ear thickness was measured on the left ear of the mice by a micrometer screw. The measurement was repeated on day 12. The ear thickness of the left ear of the mice in the groups 1 and 2 was measured concurrently. The left ear of all the mice was compared with the right one to establish the presence or absence of erythema caused by the TPA-treatment and the succeeding treatment with 2,4-DCBA and the control substance or no treatment at all as in groups 1 and 2. The body weight of the mice was determined on day 12 and compared with the body weight on day 1. The results thus obtained appear from Table 1.

The average value for thickness of the left ear of the mice was calculated for all 4 groups and statistical calculations were made for the thickness measurements using the SAS-program (Version 6.12). The result, which is stated in table 2, shows that there is a statistically significant difference ($p<0.05$) in the thickness of the ears of mice in group 2 and the mice in group 3 and group 4 in the last measurement.

By determining ear erythema it was observed that the mice in group 3 exhibited a reduced ear erythema on day 12 as compared with the mice in group 2.

By determining the body weight of the mice it could be seen that only the mice in group 1 had gained weight during the experiment. Weight loss was observed for the remaining groups, smallest in group 3. The weight loss in group 4 was a factor 4 higher compared to group 3, cf. table 3.

TABLE 1

| Animal number | Ear thickness day 11, (μm) | Ear thickness day 12, (μm) | Blushing (+/÷) day 11 | Blushing (+/÷) day 12 | Body weight day 1, (g) | Body weight day 12, (g) |
|---|---|---|---|---|---|---|
| 1 | 20 | 22 | — | — | 21 | 21 |
| 2 | 21 | 21 | — | — | 19 | 20 |
| 3 | 23 | 22 | — | — | 19 | 20 |
| 4 | 21 | 22 | — | — | 19 | 19 |
| 5 | 21 | 21 | — | — | 20 | 21 |
| 6 | 33 | 20 | — | — | 19 | 19 |
| 7 | 60 | 59 | + | + | 20 | 21 |
| 8 | 70 | 63 | + | + | 20 | 20 |
| 9 | 71 | 63 | + | + | 21 | 20 |
| 10 | 64 | 56 | + | + | 20 | 19 |
| 11 | 69 | 50 | + | + | 21 | 20 |
| 12 | 60 | 52 | + | + | 21 | 19 |
| 13 | 65 | 36 | + | (+) | 19 | 19 |
| 14 | 60 | 41 | + | (+) | 22 | 21 |
| 15 | 55 | 42 | + | (+) | 21 | 20 |
| 16 | 65 | 42 | + | (+) | 19 | 19 |
| 17 | 62 | 42 | + | (+) | 21 | 20 |
| 18 | 70 | 49 | + | (+) | 20 | 20 |
| 19 | 31 | 32 | — | — | 20 | 18 |
| 20 | 31 | 30 | — | — | 20 | 18 |
| 21 | 28 | 32 | — | — | 20 | 18 |
| 22 | 32 | 26 | — | — | 22 | 19 |
| 23 | 34 | 30 | — | — | 19 | 18 |
| 24 | 28 | 28 | — | — | 20 | 19 |

(+) denotes reduced erythema as compared with group 2

TABLE 2

| Group | Day 11 | | | | Day 12 | | | |
|---|---|---|---|---|---|---|---|---|
| | Average | S.D. | N | p | Average | S.D. | N | p |
| 1 | 21.3 | 1.0 | 6 | A | 21.3 | 0.8 | 6 | A |
| 2 | 65.7 | 5.0 | 6 | C | 57.2 | 5.5 | 6 | D |
| 3 | 52.8 | 5.1 | 6 | C | 42.0 | 4.1 | 6 | C |
| 4 | 30.7 | 2.3 | 6 | B | 29.2 | 2.3 | 6 | B |

Average values attached to the various letters are significant differences ($p < 0.05$)
S.D. = Standard deviation
N = Number of animals

TABLE 3

| | Total weight day 1 and day 12 | | | |
|---|---|---|---|---|
| Group | Day 1 | Day 12 | Deviation | % increase/loss |
| 1 | 117 g | 120 g | +3 g | +2.6 |
| 2 | 123 g | 119 g | −4 g | −3.3 |
| 3 | 122 g | 119 g | −3 g | −2.5 |
| 4 | 121 g | 110 g | −11 g | −9.1 |

What is claimed is:

1. A method for reducing inflammation of an inflamed area of a person which comprises the steps of:

(a) providing an anti-inflammatory preparation composed of a mixture consisting essentially of 2,4-DCBA and a bioadhesive material, and (b) applying said anti-inflammatory preparation to the inflamed area in an amount to reduce said inflammation, said 2,4-DCBA being applied in an up to 1% concentration, thus not causing inflammation that would occur at a concentration of more than 1%, and said bioadhesive material acting to retain said preparation on said inflamed area for a prolonged period of time.

2. A method according to claim 1, wherein said inflamed area is skin.

3. A method according to claim 2, wherein inflamed area is caused by trauma, sunburn, heat eczema, contact allergy, psoriasis, erysipelas, acne, nail inflammation, cuts, burns, insect bites, insect stings or pruritus.

4. A method according to claim 3, wherein said inflamed area is caused by contact allergy.

5. A method according to claim 4, wherein said bioadhesive material is carboxymethyl cellulose.

6. A method according to claim 2, wherein said bioadhesive agent is a hydrocolloid selected from the group consisting of carboxymethyl cellulose, Carbopol, tragacanth, karaya gum, sodium alginate, gelatin, methylcellulose and gum arabic.

7. A method according to claim 1, wherein said inflamed area is mucosa.

8. A method according to claim 7, wherein said inflamed area is caused by periodontitis, eruption of wisdom teeth, teeth extraction, insufficient dental hygiene, periodontal abscesses or prosthesis.

9. A method according to claim 2, wherein said bioadhesive material is a mucoadhesive hydrocolloid selected from the group consisting of carboxymethyl cellulose, Carbopol, tragacanth, karaya gum, sodium alginate, gelatin, methylcellulose and gum arabic.

10. A preparation for application to an inflamed area of a person so as to reduce inflammation and not cause inflammation, said preparation consisting essentially of 2,4-DCBA as a sole anti-inflammatory agent in an amount of 0.05 to 2 wt. %, a hydrocolloid bioadhesive agent in an amount of 0.1 to 10 wt. %, and water in an amount of 90–99 wt. %.

11. A preparation according to claim 10, wherein said hydrocolloid bioadhesive agent is selected from the group consisting of carboxymethyl cellulose, Carbopol, tragacanth, karaya gum, sodium alginate, gelatin, methylcellulose and gum arabic.

12. A preparation according to claim 11, wherein said hydrocolloid bioadhesive is carboxymethyl cellulose.

* * * * *